(12) United States Patent
Tohse et al.

(10) Patent No.: US 10,188,847 B2
(45) Date of Patent: Jan. 29, 2019

(54) MEDICAL DEVICE (71) Applicant: HI-LEX CORPORATION, Hyogo (JP)

(72) Inventors: Hidekazu Tohse, Hyogo (JP); Junji Fujita, Hyogo (JP); Akihiro Ametani, Hyogo (JP); Akihisa Ishii, Tokyo (JP); Shinichi Hori, Osaka (JP); Atsushi Hori, Osaka (JP)

(73) Assignee: HI-LEX CORPORATION (JP)

( * ) Notice: Subject to any disclaimer, the term of this patent is extended or adjusted under 35 U.S.C. 154(b) by 75 days.

(21) Appl. No.: 15/107,975

(22) PCT Filed: Dec. 26, 2014

(86) PCT No.: PCT/JP2014/084684
§ 371 (c)(1),
(2) Date: Jun. 24, 2016

(87) PCT Pub. No.: WO2015/099168
PCT Pub. Date: Jul. 2, 2015

(65) Prior Publication Data
US 2016/0317799 A1  Nov. 3, 2016

(30) Foreign Application Priority Data
Dec. 27, 2013 (JP) .................. 2013-272932

(51) Int. Cl.
*A61M 39/10* (2006.01)
*A61M 5/14* (2006.01)
(Continued)

(52) U.S. Cl.
CPC ... *A61M 39/1011* (2013.01); *A61B 17/12186* (2013.01); *A61M 5/1407* (2013.01);
(Continued)

(58) Field of Classification Search
CPC .. A61M 5/345; A61M 39/10; A61M 39/1011; A61M 2039/1077;
(Continued)

(56) References Cited

U.S. PATENT DOCUMENTS 1,558,829 A * 10/1925 Brody ................... A61M 5/347
604/241
5,285,776 A   2/1994 Bertram
(Continued)

FOREIGN PATENT DOCUMENTS

FR   2775436    9/1999
JP   06277298   10/1994
(Continued)

OTHER PUBLICATIONS

Supplementary European Search Report, European Application No. 14874875, dated Aug. 11, 2017.
(Continued)

Primary Examiner — Nathan R Price
Assistant Examiner — Anh Bui
(74) Attorney, Agent, or Firm — Perman & Green, LLP (57) ABSTRACT A medical device which absorbs a difference in dimension between the members, can be applied to an existing device without generating a dead space in a flow path of a therapeutic substance when administrating the therapeutic substance, and is high in versatility. The medical device includes a feeding member, a connected member and a joint member, and the joint member includes an inner tapered portion and an outer tapered portion, the joint member is configured so that the tip end of the joint member is located on the inner tapered connecting portion when the joint member is connected to the hub.

5 Claims, 7 Drawing Sheets (51) Int. Cl.
  *A61M 5/145* (2006.01)
  *A61M 25/00* (2006.01)
  *A61M 5/34* (2006.01)
  *A61B 17/12* (2006.01)

(52) U.S. Cl.
  CPC .......... *A61M 5/1452* (2013.01); *A61M 5/345* (2013.01); *A61M 25/0097* (2013.01); *A61M 39/10* (2013.01); *A61B 2017/1205* (2013.01); *A61M 2039/1077* (2013.01); *A61M 2039/1083* (2013.01); *A61M 2039/1088* (2013.01)

(58) Field of Classification Search
  CPC .. A61M 2039/1088; A61M 2039/1083; A61M 25/0097
  See application file for complete search history.

(56) References Cited

U.S. PATENT DOCUMENTS

| | | |
|---|---|---|
| 5,336,192 A | 8/1994 | Palestrant |
| 6,152,913 A | 11/2000 | Feith et al. |
| 6,565,551 B1 | 5/2003 | Jones et al. |
| 6,699,222 B1 | 3/2004 | Jones et al. |
| 2012/0029465 A1 | 2/2012 | Wu et al. |
| 2013/0178806 A1 | 7/2013 | Felix-Faure et al. |
| 2013/0264266 A1 | 10/2013 | Shick et al. |
| 2013/0267907 A1 | 10/2013 | Wu et al. |

FOREIGN PATENT DOCUMENTS

| | | |
|---|---|---|
| JP | 2002503991 | 2/2002 |
| JP | 2012110669 | 6/2009 |
| JP | 4357067 | 11/2009 |
| JP | 2013521093 | 6/2013 |
| JP | 2013535277 | 9/2013 |
| WO | 9856435 | 12/1998 |
| WO | 2004032707 | 4/2004 |
| WO | 2011110888 | 9/2011 |
| WO | 2012015781 | 2/2012 |

OTHER PUBLICATIONS

International Preliminary Report on Patentability, International Application No. PCT/JP2014/084684, dated Jun. 28, 2016.
International Search Report, International Application No. PCT/JP2014/084684, dated Mar. 24, 2015.

\* cited by examiner

MEDICAL DEVICE

CROSS REFERENCE TO RELATED APPLICATIONS

This application is the National Stage of International Application No. PCT/JP2014/084684 having International Filing Date, 26 Dec. 2014, which designated the United States of America, and which International Application was published under PCT Article 21 (2) as WO Publication No. 2015/099168 A1, and which claims priority from, and the benefit of, Japanese Application No. 2013-272932, filed on 27 Dec. 2013, the disclosures of which are incorporated herein by reference in their entireties.

BACKGROUND

1. Field

The presently disclosed embodiment relates to a medical device for introducing a therapeutic substance into a body, particularly to a medical device to be used for operation using a catheter.

2. Brief Description of Related Developments

In a therapeutic method for introducing a therapeutic substance into a body, vascular embolization, for example, arterial embolization for treatment of hepatocellular carcinoma and the like has been used. In such treatment, in order to cut off feeding of nutrition to cancer cells, a blood vessel is clogged with an intravascular embolization substance to kill the cancer cells.

Figure 7:
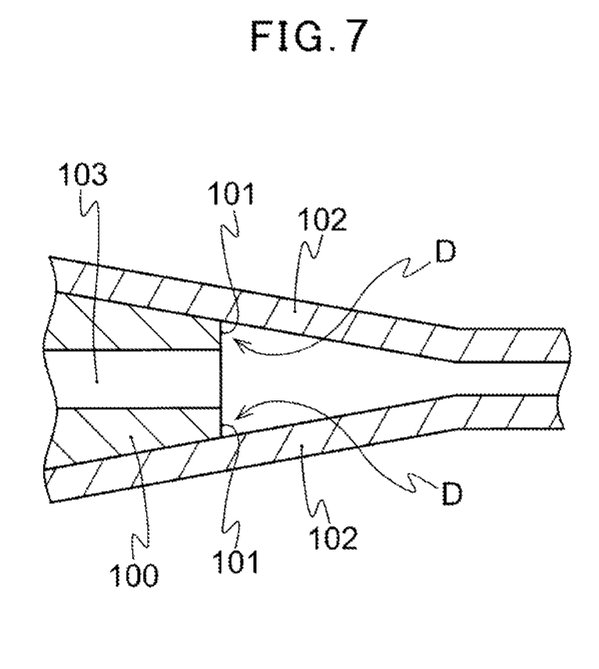
FIG. 7 is a sectional view illustrating conventional connection of a syringe with a catheter hub.
Figure 8:
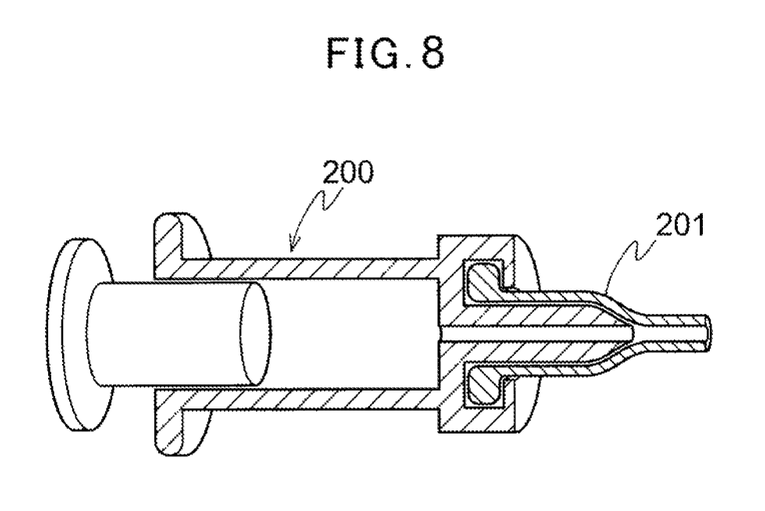
FIG. 8 is a partial sectional view illustrating conventional connection of a syringe with a catheter hub.

Introduction of such a therapeutic substance into a body cavity is performed by connecting a feeding member such as a syringe for feeding a therapeutic substance containing the therapeutic substance including an intravascular embolization substance with a catheter hub, and inserting the catheter in the blood vessel up to a vicinity of an affected part. The syringe and the catheter hub are generally connected by luer taper connection, and the syringe is inserted into the catheter hub to be fitted and fixed. As shown in FIG. 7, the end portion of the syringe at the distal end side generally has an end face 101 facing an axial direction of the syringe 100, and the syringe is connected to the catheter hub such that a flow channel 103 at the end portion of the syringe at the distal end side is separated front an inner surface of the catheter hub 102. Therefore, it results in an annular dead space D lateral to the flow channel 103 with respect to an axial direction of the syringe 100 as a space between the end face 101 of the syringe 100 and the inner surface of the catheter hub 102. As shown in FIG. 7, such a dead space D is generated by a step formed along the flow channel between the end face 101 of the syringe 100 and the tapered surface of the catheter hub 102. This step causes a problem in which the therapeutic substance such as an intravascular embolization substance remains in the dead space B due to generation of turbulence in the dead space D of a flow path of the therapeutic substance when injecting the therapeutic substance from the syringe 100. Further, this remaining therapeutic substance in the dead space D causes a problem such that the therapeutic substance is administrated to a patient only in an amount smaller than a predetermined amount required for the treatment; the remaining therapeutic substance is flowed into a body cavity at once to temporarily increase the concentration more than a predetermined value; the remaining therapeutic substance flows into a body cavity in the following operation and is delivered to a portion other than the originally targeted port ion; and an excess amount of therapeutic substance is required for the purpose of administrating to a patient a predetermined amount necessary for the treatment.

Figure 9:
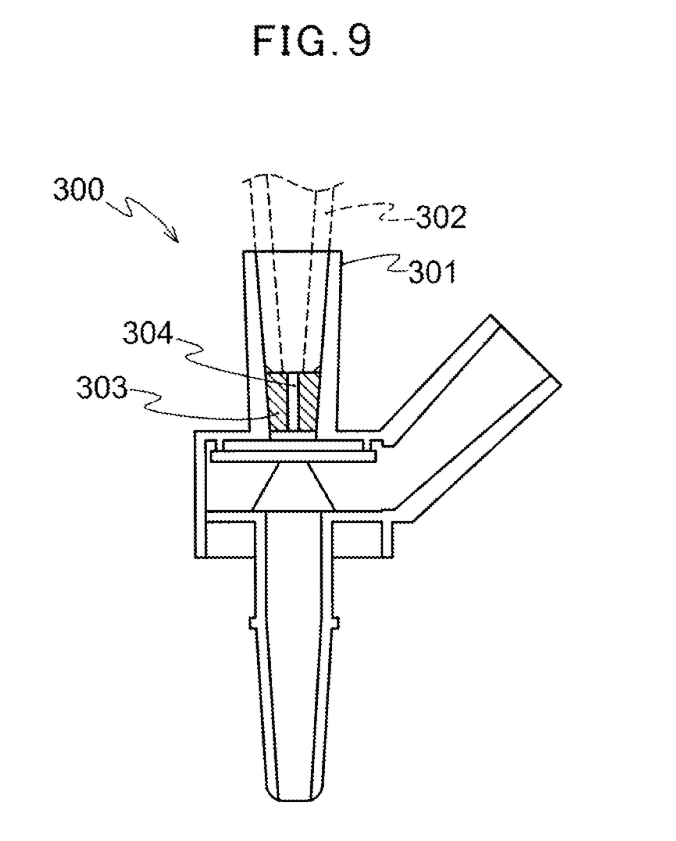
FIG. 9 is a view illustrating conventional luer taper connection.

From the viewpoint of the mentioned problems, in a system for administration of a therapeutic substance into a body cavity including administration of a therapeutic substance comprising an intravascular embolization substance into an affected part for cancer treatment, various attempts have been performed in order to eliminate a dead space resulting from luer taper connection. For example, in Japanese Patent No. 2002-503991, there is disclosed a syringe 200 having, at its distal end, a tapered outer wall adapted to an inner wall shape of a micro catheter luer hub 201. In Japanese Patent No. 4357067, there is disclosed, as shown in FIG. 9, a structure where a gap in a connected portion 301 is filled with a filling body 303 when a male adapter 302 is fitted into the connected portion 301 being a female adapter of a connector 300. This filling body 303 is formed from a material being excellent in flexibility and cushioning properties such as a soft synthetic resin or a silicone rubber, and is configured so that the male adapter 302 is connectable even in the case of the distal end of the male adapter 302 is extended.

SUMMARY

However, in the structure of Japanese Patent No. 2002-503991, unless both of the syringe 200 and the micro catheter luer hub 201 are produced precisely, there is a high possibility that a dead space is generated due to a difference in dimension between the distal end of the syringe 200 and the inner wall of the catheter luer hub 201. Also, in the structure of Japanese Patent No. 2002-503991, it cannot be used in combination with other syringe and micro catheter luer hub having different diameter, length or the like and there is no versatility.

In the case of Japanese Patent No. 4357067, the filling body 303 needs to be put in an inner cavity of the connector 300 beforehand and therefore, is hardly applied to an existing device. In addition, when the male adaptor 302 is pushed into the connected portion 301, the filling body 303 may be deformed and the flow channel 304 may also be deformed. If the flow channel 304 is deformed, a dead space such as a step may be produced in the flow channel 304 and in the worst case, the flow channel 304 may be blocked.

In the light of the above-mentioned problems, an object of the presently disclosed embodiment is to provide a medical device which absorbs a difference in dimension between the members, inhibits a dead space from being generated in a flow path of a therapeutic substance when the therapeutic substance is administrated, can be applied to an existing device and has high versatility.

The medical device of the presently disclosed embodiment is a medical device comprising a feeding member comprising a tubular body portion being capable of containing a therapeutic substance to be fed into a body cavity and a tubular connecting portion provided at one end of the body portion and having a male luer tapered portion and an opening provided at a distal end of the male luer tapered portion to feed the therapeutic substance contained in the body portion; a connected member having a flow channel through which the therapeutic substance fed from the feeding member passes and provided with a hub having an inner tapered connecting portion including a female luer tapered portion; and a joint member connected to the tubular connecting portion of the feeding member and the hub of the connected member and having a communication channel for communicating the tubular connecting portion of the feeding member with the flow channel of the connected member, and the device is characterized in that the joint member comprises an inner tapered portion for connecting to the male luer tapered portion, an outer tapered portion for connecting to the female luer tapered portion, and an opening at the side of the connected member located at a tip end of the outer tapered portion for feeding the therapeutic substance from the feeding member to the connected member, and when the joint member is connected to the hub, the joint member is configured so as to allow the inner end portion of the opening at the side of the connected member to be disposed in proximity with and along the tapered surface of the inner tapered connecting portion so that the tip end of the joint member is located on the inner tapered connecting portion.

It is preferable that the joint member has an abutting face to which an end face of the tubular connecting portion abuts when the tubular connecting portion is pressed into the joint member along the inner tapered portion, and the inner surface of the communication channel and the inner surface of the tubular connecting portion have substantially the same diameter at a connecting place.

It is preferable that the joint member is formed from a resin or a metal.

It is also preferable that a lock mechanism is provided to the feeding member and/or the joint member, and when the feeding member and the joint member are locked by means of the lock mechanism, the end face of the tubular connecting portion abuts onto the abutting face of the joint member.

Further it is preferable that the feeding member is a syringe, a three-way cock or a four-way cock, and the connected member is a catheter.

Furthermore it is preferable that the therapeutic substance is an intravascular embolization substance, the medical device is a medical device for vascular embolization for injecting the intravascular embolization substance into a body cavity, and the catheter is configured to be capable of feeding from the distal end of the catheter a mixed liquid contained in the syringe and comprising the intravascular embolization substance and a medicine.

According to the medical device of the presently disclosed embodiment, a difference in dimension between the members can be absorbed, generation of a dead space in a flow path of a therapeutic substance can be inhibited when administrating the therapeutic substance, the device can be applied to an existing device, and versatility is high.

DETAILED DESCRIPTION

A medical device of the presently disclosed embodiment is then explained below in detail in reference to the attached drawings.

The medical device of the presently disclosed embodiment is used to form a continuous path by jointing a plurality of members when feeding a therapeutic substance into a body cavity such as a blood vessel or an organ and feed the therapeutic substance into the body cavity through the continuous path. In aspects described below, explanation is made using a medical device for embolization as an example. However, the medical device is not limited to one for embolization as far as it is a medical device feeding a therapeutic substance into a body cavity and having effects described below. Further, with respect to a therapeutic substance to be fed to a body cavity, in aspects described below, explanation is made using a therapeutic substance comprising resin particles being an example of an intravascular embolization substance. However, the therapeutic substance is not limited particularly as far as it is one having effects described below, and it is possible to use a therapeutic substance depending on a symptom requiring medical treatment.

Figure 1:
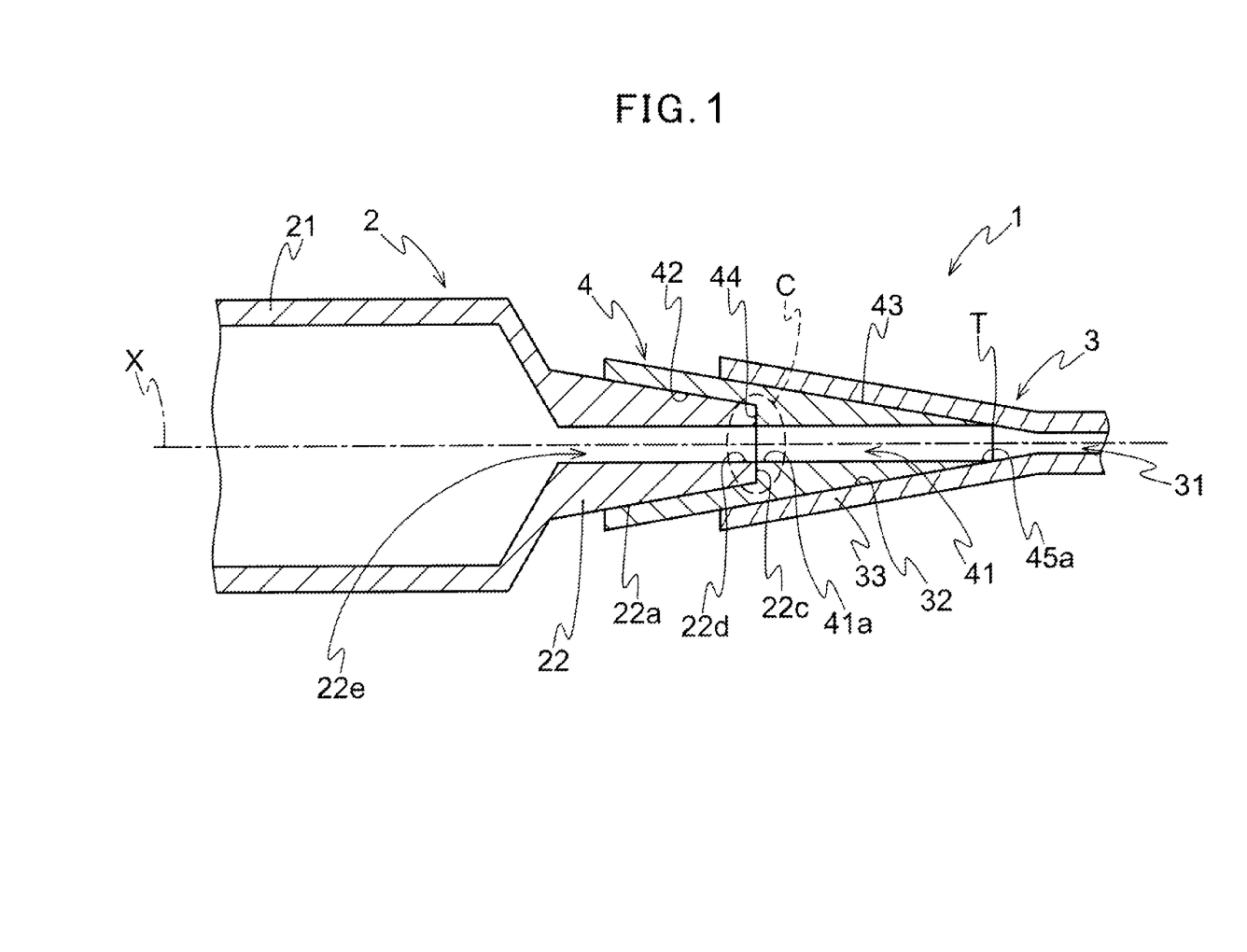
FIG. 1 is a sectional view illustrating a medical device of the presently disclosed embodiment being in a jointed state.
Figure 2:
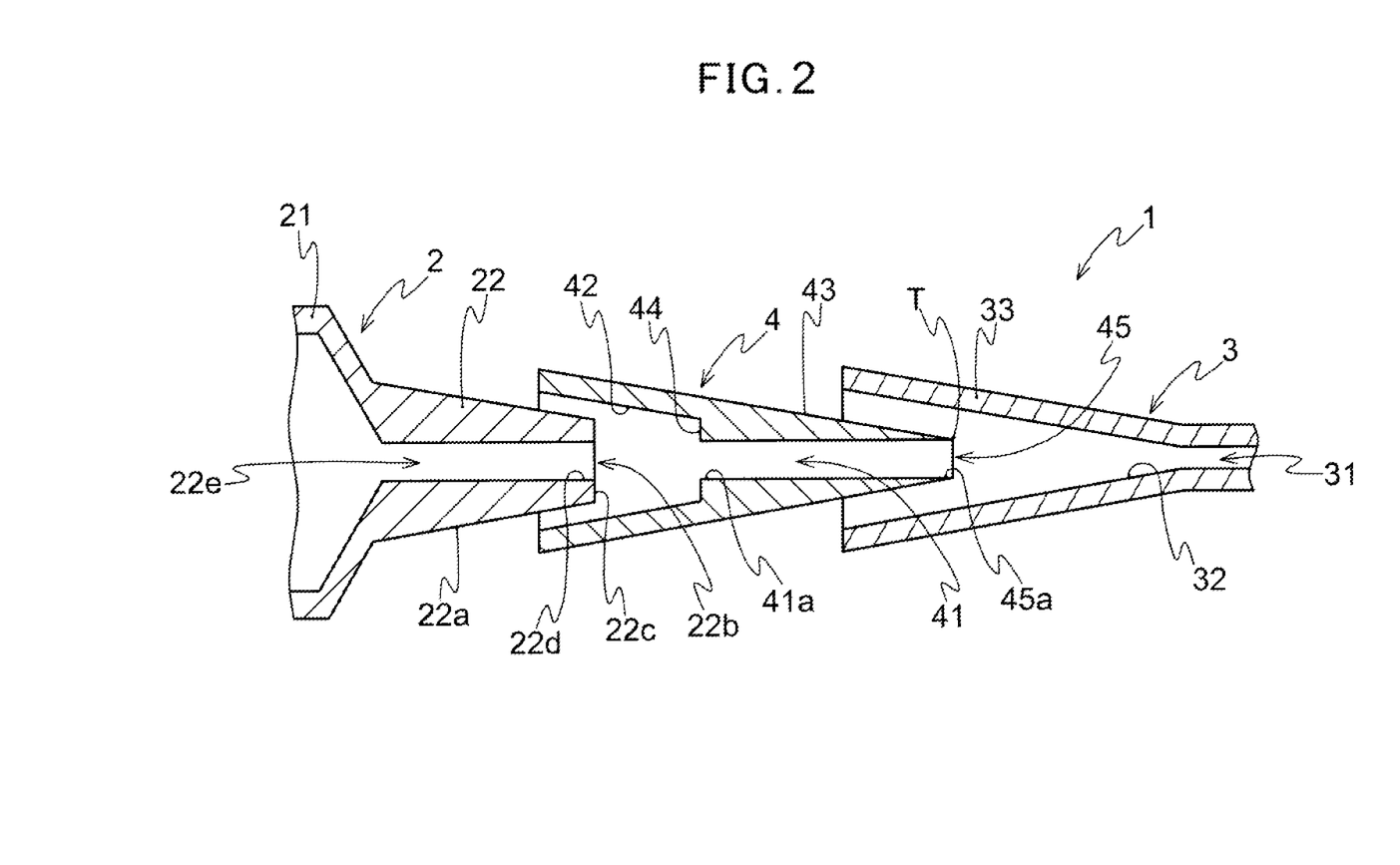
FIG. 2 is a sectional view illustrating a medical device of the presently disclosed embodiment before being jointed.

As shown in FIGS. 1 and 2, the medical device 1 of the presently disclosed embodiment comprises a feeding member 2 for feeding a therapeutic substance into a body cavity, and a connected member 3 being connected indirectly to the feeding member to feed the therapeutic substance fed from the feeding member into a body cavity. The feeding member 2 is a member for feeding the therapeutic substance toward the connected member 3. The feeding member 2 may be a member being capable of feeding the therapeutic substance from the feeding member to the connected member 3. The feeding member 2 may be a supply source of the therapeutic substance fed into a body cavity, or the therapeutic substance may be fed to the feeding member 2 from an another member not shown in drawings and then fed to the connected member 3 using the feeding member 2 as a relay member. The connected member 3 is connected indirectly to the feeding member 2 and guides the therapeutic substance fed from the feeding member 2 into a body cavity. The connected member 3 may be configured so as to feed the therapeutic substance from the connected member 3 directly into a body cavity, or may be configured so as to feed the therapeutic substance into a body cavity via an another member not shown in drawings.

As shown in FIGS. 1 and 2, the feeding member 2 is provided with a tubular body portion 21 being capable of containing the therapeutic substance to be fed into a body cavity and a tubular connecting portion 22 provided at one end of the body portion 21 and having a male luer tapered portion 22a and an opening 22b (see FIG. 2) provided at a distal end of the male luer tapered portion 22a and used to feed the therapeutic substance contained in the body portion 21. The tubular body portion 21 contains the therapeutic substance therein. In FIG. 1, while the tubular body portion 21 is shown as a tubular body portion 21 having uniform outer and inner diameters in an axial direction, the shape of the body portion 21 is not limited to the one shown in the drawing. As shown in FIGS. 1 and 2, the tubular connecting portion 22 is provided at one end of the body portion 21. The tubular connecting portion 22 has the male luer tapered portion 22a at the outer surface side of the tubular connecting portion 22. The tubular connecting portion 22 has the opening 22b at a free end side of the tubular connecting portion 22 so as to be able to discharge the therapeutic substance contained inside of the body portion 21. The therapeutic substance contained in the body portion 21 is fed toward the connected member 3 side through a feeding channel 22e formed inside the tubular connecting portion 22 and the opening 22b. The tubular connecting portion 22 has the male luer tapered portion 22a and is connected to a joint member 4 described below through luer taper connection to be fixed. The male luer tapered portion 22a is formed on the entire tubular connecting portion 22 in an axial direction in FIGS. 1 and 2. However, as far as the tubular connecting portion 22 can be connected to the joint member 4 through luer taper connection, the male luer tapered portion 22a needs not to be formed on the entire tubular connecting portion 22 in an axial direction, and may be formed on a part of the tubular connecting portion 22 in an axial direction. It should be noted that a taper angle of the male luer tapered portion 22a is not limited to an angle shown in the drawing as far as the luer taper connection can be executed.

As shown in an aspect described below, for example, a syringe is used as the feeding member 2. The feeding member 2 is not limited to a syringe as far as it has the body portion 21 and the tubular connecting portion 22 and can be connected to the joint member 4 by luer taper connection. The feeding member 2 may be, for example, other medical tools such as a three-way cock and a four-way cock, or other medical tools such as a transfusion bag having a flexible body portion. Further, while in FIGS. 1 and 2, the tubular connecting portion 22 is disposed coaxially on a central axis of the tubular body portion 21, it may be disposed being deviated from the central axis of the tubular body portion 21 like an eccentric-type syringe.

Figure 3:
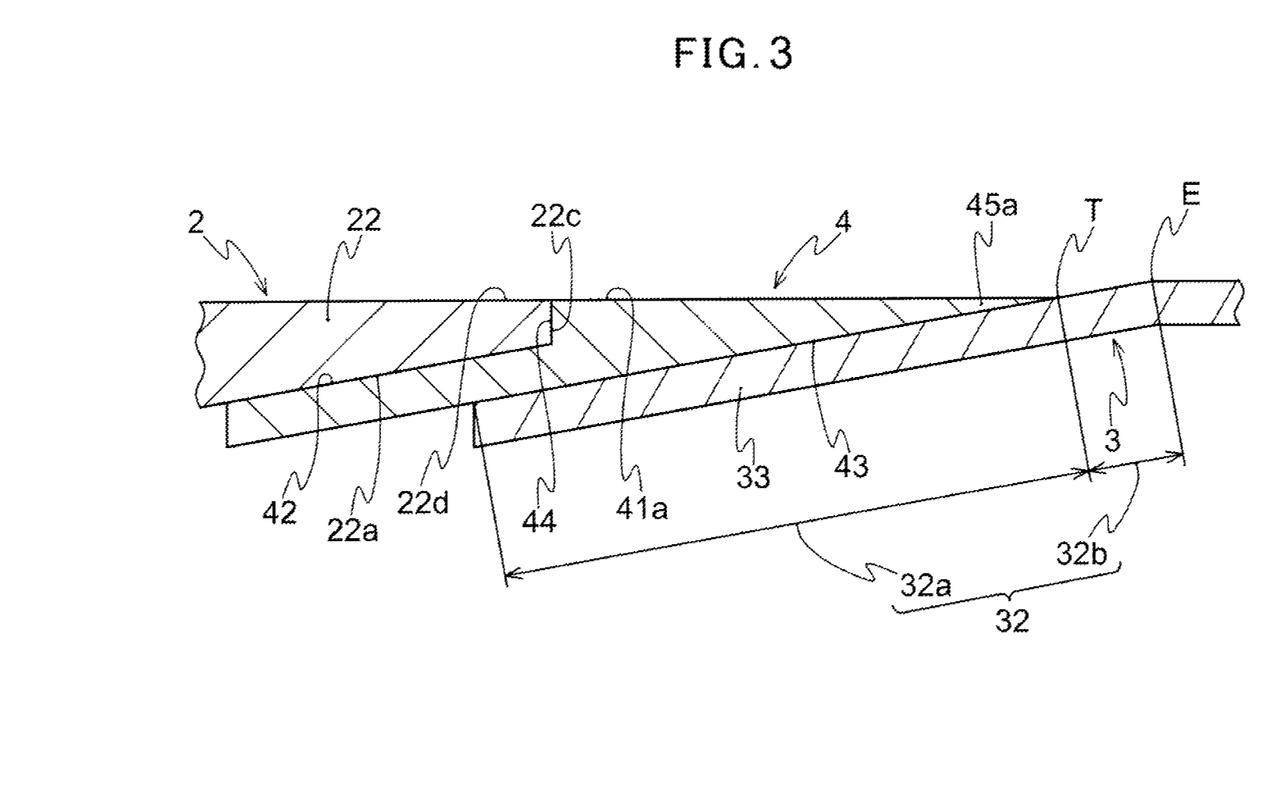
FIG. 3 is an enlarged sectional view of a connecting place of a medical device of FIG. 1.

The connected member 3 has a flow channel 31 through which the therapeutic substance fed from the feeding member 2 passes, and a hub 33 having an inner tapered connecting portion 32 including a female luer tapered portion 32a (see FIG. 3). The connected member 3 is a member indirectly connected to the feeding member 2 through the joint member 4 described later, and functions as a path for feeding the therapeutic substance fed from the feeding member 2 to a further downstream side via the flow channel 31. Specifically, for example, a catheter having a catheter hub is used as the connected member 3 as explained in an aspect described below. However, the connected member 3 may be a member provided with the flow channel 31 and the hub 33 having the inner tapered connecting portion 32, and is not limited to the catheter as far as luer taper connection can be carried out. Other medical tools such as a three-way cock and Y-connector which can be connected by luer taper connection may be used as the connected member 3. The inner tapered connecting portion 32 is a portion to be connected to the joint member 4 described below by luer taper connection, and is subjected to luer taper connection with the joint member 4 via the female luer tapered portion 32a. As shown in FIG. 3, the inner tapered connecting portion 32 further includes an inner tapered surface 32b which is not in contact with the joint member 4 in the drawing in addition to the female luer tapered portion 32a. Thus, the female luer tapered portion 32a may be a part of the inner tapered connecting portion 32, or the entire inner tapered connecting portion 32 may be the female luer tapered portion 32a. Further, in the inner tapered connecting portion 32, a portion other than the female luer tapered portion 32a may be the inner tapered surface 32b having the same taper angle as the female luer tapered portion 32a, or may be the inner tapered surface 32b having a taper angle different from that of the female luer tapered portion 32a.

In a conventional medical device, for example, in the case of connecting a syringe to a catheter hub, as shown in FIG. 7, the syringe 100 and the catheter hub 102 are connected by luer taper connection using a male luer taper and a female luer taper formed on the syringe 100 and the catheter hub 102, respectively. In such a case, as mentioned above, there is a problem that the dead space D is generated between the end face 101 of the syringe 100 and the female luer taper of the catheter hub 102 due to a step, thereby causing a therapeutic substance to remain in the dead space D. The feeding member 2 to be used in the presently disclosed embodiment generally has an end face 22c being vertical to an axial direction of the tubular connecting portion 22 at the free end side of the tubular connecting portion 22 as shown in FIGS. 1 to 3 in accordance with standards for medical appliances. Therefore, in the case of using the feeding member 2 in which the tubular connecting portion 22 has an end face 22c, when simply connecting the feeding member 2 to the connected member 3 by luer taper connection, there arises a problem with a dead space. In order to solve such a problem, the device 1 for medical treatment of the presently disclosed embodiment is provided with the joint member 4 between the feeding member 2 and the connected member 3.

The joint member 4 is, as shown in FIG. 1, connected to the tubular connecting portion 22 of the feeding member 2 and the hub 33 of the connected member 3. Further, the joint member 4 has a communication channel 41 communicating the tubular connecting portion 22 of the feeding member 2 with the flow channel 31 of the connected member 3. The joint member 4 is a member for connecting the feeding member 2 to the connected member 3. As shown in FIGS. 1 to 3, the joint member 4 is provided with an inner tapered portion 42 for connecting to the male luer tapered portion 22a of the tubular connecting portion 22 for connection to the tubular connecting portion 22 of the feeding member 2. It is preferable that the joint member 4 is connected to the tubular connecting portion 22 in a liquid-tight manner. However it is enough to connect them so as to enable the therapeutic substance to be fed from the feeding member 2 to the joint member 4 without any problem. For example, the liquid-tight connection may be made by bringing the male luer tapered portion 22a into contact with the inner tapered portion 42 in a liquid-tight manner or another member such as a sealing member may be provided on an outer surface of the male luer tapered portion 22a for liquid-tight connection of the inner tapered portion 42. Further, for example, the feeding member 2 may be connected to the joint member 4 so that physiological saline is filled between the male luer tapered portion 22a and the inner tapered portion 42 and the therapeutic substance is fed from the feeding member 2 to the joint member 4. Further, for the connection to the hub 33 of the connected member 3, the joint member 4 has the outer tapered portion 43 for connecting to the female luer tapered portion 32a of the hub 33. Furthermore, the joint member 4 is provided with an opening 45 (see FIG. 2) at the side of the connected member for feeding the therapeutic substance from the feeding member 2 to the connected member 3 and the opening 45 is located at a tip end of the outer tapered portion 43. It is preferable that the joint member 4 is connected to the connected member 3 in a liquid-tight manner. However it is enough to connect them so as to enable the therapeutic substance to be fed from the opening 45 at the side of the connected member toward the connected member 3 without any problem. For example, the liquid-tight connection may be made by bringing the tip end of the outer tapered portion 43 of the joint member 4 into contact with the inner tapered connecting portion 32 of the hub 33 in a liquid-tight manner, or another member such as a sealing member may be provided on the outer surface of the outer tapered portion 43 for liquid-tight connection of the inner tapered connecting portion 32. Further, for example, the joint member 4 may be connected to the hub 33 so that physiological saline is filled between the inner tapered connecting portion 32 of the hub 33 and the outer tapered portion 43 and the therapeutic substance is fed to the connected member 3 side.

Furthermore, as shown in FIGS. 1 and 3, when the joint member 4 is connected to the hub 33, the joint member 4 is configured so as to allow the inner end portion 45a of the opening 45 at the side of the connected member to be disposed in proximity with and along the tapered surface of the inner tapered connecting portion 32 so that the tip end T of the joint member 4 is located on the inner tapered connecting portion 32. More specifically, as shown in FIGS. 1 and 3, in regard to the joint member 4, the inner surface portion at the end of the communication channel 41 (an edge of the opening 45 at the side of the connected member) which is an outlet of the therapeutic substance is configured so as to be disposed along the inner tapered connecting portion 32. The joint member 4 is connected to the hub 33 so that the inner end portion 45a is located in the proximity with the tapered surface of the inner tapered connecting portion 32 in a vertical direction with respect to the axial direction of the joint member 4 in order not to generate a step such as a concave portion causing a problem with retention of the therapeutic substance between the tip end T of the joint member 4 and the inner tapered connecting portion 32 in a vertical direction with respect to a flow direction of the therapeutic substance (outward in a radial direction). The tip end T of the joint member 4 is formed in a tapered shape so that an acute angle is formed at the connected member 3 side with the outer tapered portion 43 and the inner surface 41a of the communication channel 41. The jointing portion 4 and the connected portion 3 are connected by luer taper connection by the above-mentioned configuration. Therefore, generating of a dead space between the tip end T of the joint member 4 and the inner tapered connecting portion 32 is inhibited. Therefore, retention of the therapeutic substance at the connecting place of the joint member 4 and the connected portion 3 can be inhibited. It should be noted that the tip end T is not necessarily formed into an acute angle shape since the retention hardly occurs when the thickness of the tip end T of the joint member 4 is sufficiently thin.

In the medical device 1 of the presently disclosed embodiment, the joint member 4 is, as described above, provided with the inner tapered portion 42 and the outer tapered portion 43, and the tip end T of the joint member 4 is disposed on the inner tapered connecting portion 32. Therefore, a dimensional difference between the members can be absorbed by the joint member 4. Further, generation of a dead space on a flow path of the therapeutic substance and retention of the therapeutic substance on the dead space can be inhibited. Thereby, it is possible to administrate an accurate amount of the therapeutic substance to a patient. The use of the joint member 4 is very significant, especially, from the viewpoint that an end face 22c where a dead space is easily generated is formed at a free end of the feeding member 2 such as a syringe generally used for medical application or from the viewpoint that it is difficult to modify the shapes of the feeding member 2 and the connected member 3 due to a problem on cost and standard thereof. In the medical device 1 of the presently disclosed embodiment, it is not necessary to use a special feeding member 2 and connected member 3 by using the joint member 4, and the structures of the feeding member 2 and the connected member 3 need not be modified for inhibiting a dead space. Therefore, the medical device 1 can be applied to existing feeding member 2 and connected member 3. Accordingly, not only a problem with a dead space can be inhibited but also the medical device 1 provides a very high versatility and low cost. While in the drawings, the joint member 4 is shown as a connector, it is not limited thereto, and may be a three-way cock. Further, the joint member 4 may have a tubular portion extending from the outer tapered portion to the tip end side thereof and having, at the end, an opening at the side of the connected portion.

Figure 5:
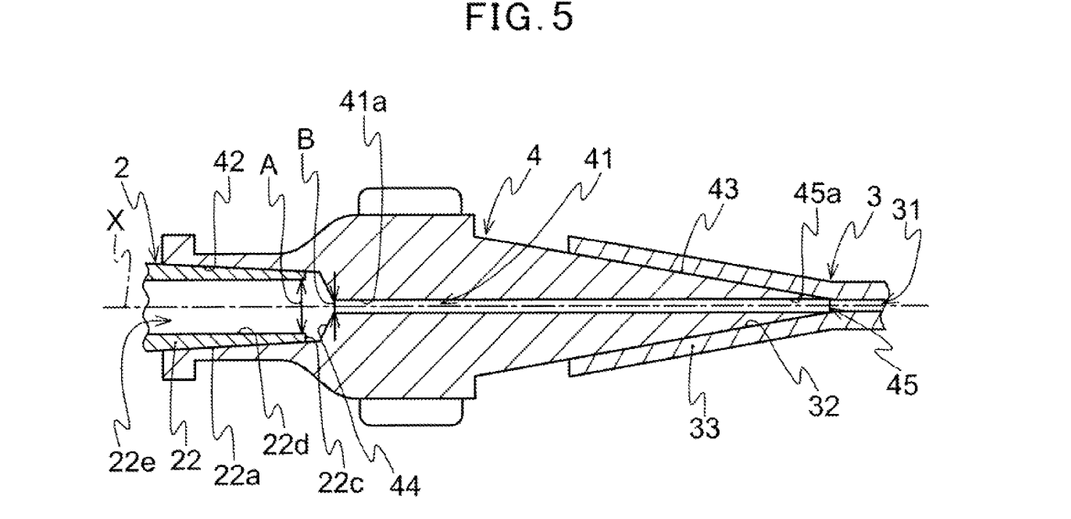
FIG. 5 is a sectional view illustrating a second aspect of a medical device of the presently disclosed embodiment.
Figure 6:
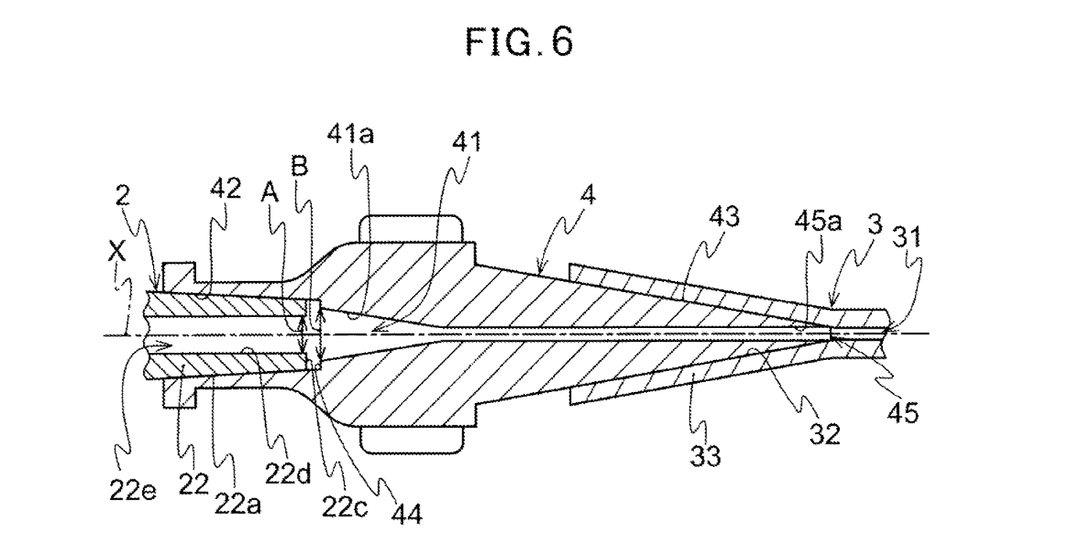
FIG. 6 is a sectional view illustrating a third aspect of a medical device of the presently disclosed embodiment.

As shown in FIGS. 1 to 3, the jointing portion 4 has an abutting face to which the end face 22c of the tubular connecting portion 22 abuts when the tubular connecting portion 22 is pressed into the joint member 4 along the inner tapered portion 42. The inner surface 41a of the communication channel 41 and the inner surface 22d of the tubular connecting portion 22 have substantially the same diameter at a connecting place C (see FIG. 1). In this aspect, as shown in FIGS. 1 to 3, the joint member 4 is configured such that an inner diameter of an end portion of the inner tapered portion 42 at the connected member 3 side is larger than an inner diameter of an end portion of the inner surface 41a of the communication channel 41 at the feeding member 2 side. Therefore, the joint member 4 has an end wall 44 connecting the end portion of the inner tapered portion 42 at the connected member 3 side to the end portion of the inner surface 41a of the communication channel 41 at the feeding member 2 side. This end wall 44 forms the abutting face. The inner tapered portion 42, the end wall 44 and the inner surface 41a are formed into a step-shape. In this aspect, as shown in FIGS. 1 to 3, the end wall 44 is formed substantially vertical to the insertion axis X (see FIG. 1) along which the feeding member 2 is inserted into the joint member 4, and abuts onto the end face 22c of the tubular connecting portion 22. When the joint member 4 and the feeding member 2 are connected to each other by luer taper connection, the end wall 44 forming the abutting face abuts onto the end face 22c of the tubular connecting portion 22 to connect the feeding channel 22e of the feeding member 2 to the communication channel 41 of the joint member 4. Since the inner surface 41a of the communication channel 41 and the inner surface 22d of the tubular connecting portion 22 have substantially the same diameter at a connecting place C (see FIG. 1) where the end wall 44 forming the abutting face is provided, the diameters of the flow paths at the feeding channel 22e and the communication channel 41 are substantially the same. In that case, generation of a turbulent flow at the connecting place C is inhibited and the therapeutic substance can be flowed smoothly. Further, even if the end face 22c is formed on the tubular connecting portion 22, a step or a dead space is hardly generated. Therefore, the therapeutic substance can be inhibited from remaining at the connecting place C between the feeding member 2 and the joint member 4. It should be noted that the inner surface 41a and the inner surface 22d do not need to have completely the same diameter as far as they have substantially the same diameter to such an extent not to cause a problem of retention of the therapeutic substance. Further, it is preferable that the end wall 44 abuts onto the end face 22c of the tubular connecting portion 22. However, the abutting is not necessarily required, for example, as shown in FIGS. 5 and 6 unless feeding of the therapeutic substance from the feeding channel 22e to the communication channel 41 is inhibited.

In this aspect, as shown in FIG. 3, the inner tapered connecting portion 32 of the connected member 3 has a female luer tapered portion 32a and an inner tapered surface 32b. It is designed such that when the joint member 4 is connected to the connected member 3, the inner tapered surface 32b does not come into contact with the outer tapered portion 43 of the joint member 4. In other word, it is designed such that the tip end T of the joint member 4 on the inner tapered connecting portion 32 is located at a position apart from the end E of the inner tapered connecting portion 32 on the flow channel 31 side toward the feeding member 2 side. In that case, even if the length of the joint member 4 from its end at the feeding member 2 side to the tip end T becomes longer than the designed dimension due to dimensional tolerance so that the position of the end T of the joint member 4 is located at the flow channel side of the connected member 3 by luer taper connection of the outer tapered portion 43 of the joint member 4 to the inner tapered connecting portion 32 of the connected member 3, the tip end T of the joint member 4 is surely located on the inner tapered connecting portion 32 (on the inner tapered surface 32b). Therefore, even in the case of dimensional tolerance, the tip end T of the joint member 4 can be inhibited from separating from the tapered surface of the inner tapered connecting portion 32, and so, generation of a dead space can be inhibited.

It should be noted that the shape of the joint member 4 is not limited to a substantially truncated cone shape as shown in FIGS. 1 to 3 as far as the joint member 4 is provided at least partly with the inner tapered portion 42 and the outer tapered portion 43 at the inner surface side and the outer surface side of the joint member 4 and the end T of the joint member 4 is located on the inner tapered connecting portion 32. The material of the joint member 4 is also not limited particularly, and it is preferable that the joint member 4 is formed from a resin or a metal. The resin or the metal is not limited particularly as long as it has defined elasticity to the extent that deformation of the communication channel 41 of the joint member 4 is not caused when the joint member 4 is jointed to the feeding member 2 and the connected member 3. For example, it is possible to use a hard resin such as polypropylene or polyethylene and a metal having no problem with toxicity to a living body. By forming the joint member 4 from a hard resin, the joint member 4 is hardly deformed when the feeding member 2 is pressed into the joint member 4 or the joint member 4 is pressed into the connected member 3 for luer taper connection. Therefore, generation of a dead space due to deformation of the communication channel 41, the end wall 44 or the tip end T of the joint member 4 can be prevented.

The inner tapered portion 42 and the male luer tapered portion 22a may be connected via luer taper connection so that the feeding member 2 can be pulled out easily from the joint member 4 when the feeding member 2 is pressed into the joint member 4. There may be a clearance between the end face 22c of the feeding member 2 and the end wall 44, if the clearance does not cause a problem with retention of the therapeutic substance when the therapeutic substance is fed from the feeding member 2 to the joint member 4 side. In such aspect, a part of the inner tapered portion 42 may be a connecting region coming into contact with the male luer tapered portion 22a, and the remaining part of the inner tapered portion 42 may be a non-connecting region where the inner surface side tapered portion 42 does not come into contact with the male luer tapered portion 22a. For example, by setting a region of the joint member 4 at the end wall 44 side to be the connecting region with the male luer tapered portion 22a, and setting a region at the feeding member 2 side from the connecting region to be the non-connecting region having an inner diameter larger than the outer diameter of the male luer tapered portion 22a, it is possible to retain the contacting area between the inner tapered portion 42 and the male luer tapered portion 22a to an extent necessary for obtaining an engaging force enabling the feeding process of the therapeutic substance from the feeding member 2. Therefore, the engaging force between the inner tapered portion 42 and the male luer tapered portion 22a due to the contact does not become too strong, and when the feeding member 2 is pressed into the joint member 4, it may be easy to move the joint member 4 to a position where the end face 22c of the tubular connecting portion 22 abuts onto the end wall 44, and it may be easy to remove the feeding member 2 from the joint member 4.

Figure 4:
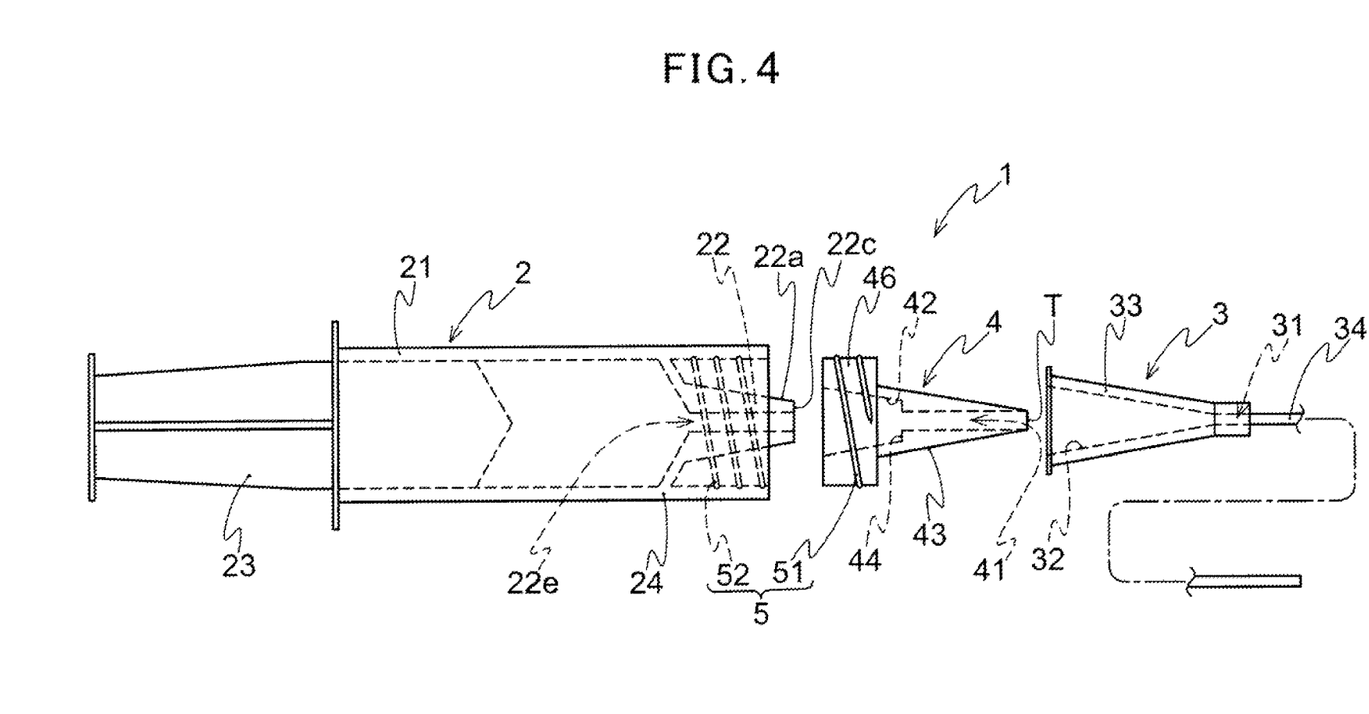
FIG. 4 is an overall view illustrating one aspect of a medical device of the presently disclosed embodiment.

As mentioned above, since the shape of the joint member 4 is not limited particularly, the portion of the joint member 4 irrelevant to the luer taper connection may have a shape different from that shown in FIGS. 1 to 3. For example, in order to securely lock the joint member 4 and the feeding member 2, a lock mechanism 5 may be provided to the feeding member 2 and/or the joint member 4 like the aspect explained below as shown in FIG. 4. In that case, as shown in FIG. 4, a locking part 51 (in FIG. 4, shown as an external thread) is provided on an end portion of the joint member 4 at the side of the feeding member 2, and a locked part 52 (in FIG. 4, shown as an internal thread) is provided on an end portion of the feeding member 2 at the side of the joint member 4 (in FIG. 4, an end portion of the body portion of the feeding member 2), thereby enabling the joint member 4 and the feeding member 2 to be locked with each other. In particular, it may be configured that the end face 22c of the tubular connecting portion 22 abuts onto the end wall 44 of the joint member 4 when the feeding member 2 and the joint member 4 are locked by means of the lock mechanism 5. In this case, it is possible to more securely prevent generation of a clearance between the end wall 44 of the joint member 4 and the end face 22c of the tubular connecting portion 22 of the feeding member 2 and to more securely prevent leakage of a liquid of a therapeutic substance. In the aspect shown in FIG. 4 explained below, while the locking part 51 and the locked part 52 of the lock mechanism 5 are locked by screwing the external thread and the internal thread. However, the lock mechanism 5 is not limited to the shown aspect, and other known lock mechanisms, for example, a recess/projection fitting structure, an engaging structure with an engaging piece and an engaged portion, and the like may be used. In the aspect shown in FIG. 4, the locked part 51 (internal thread) is provided at the feeding member 2 and the locking part 52 (external thread) is provided at the joint member 4. However, the locking part 51 and the locked part 52 may be provided reversely, for example, the locked part 51 is provided at the joint member 4, and the locking part 52 is provided at the feeding member 2.

Next, one aspect of the presently disclosed embodiment is then explained by referring to FIG. 4.

FIG. 4 shows an aspect wherein the feeding member 2 is a syringe, the connected member 3 is a catheter, and the syringe is connected to the catheter with the joint member 4. In this aspect, an amount of therapeutic substance from the syringe can be administrated precisely when the therapeutic substance is administrated by means of a catheter into a body cavity. This aspect is explained below referring to the case where the therapeutic substance is resin particles and the medical device 1 is used for arterial embolization in which the resin particles are injected into a body cavity. However, the presently disclosed embodiment is not limited to the following aspect and can be applied to medical devices used for other applications and medical devices having other structures.

As shown in FIG. 4, a syringe is used as the feeding member 2, and a mixed liquid comprising resin particles as a therapeutic substance and a medicine such as an anti-cancer agent is contained in the syringe (in the body portion 21). The syringe of this aspect has a cylindrical connecting portion 24, where the locked part 52 having an internal thread on an inner surface thereof is formed, for locking the joint member 4. Further, a locking part 51 is formed on the joint member 4 as an external thread to be screwed with the locked part 52 as an internal thread formed on the syringe. In this aspect, as shown in FIG. 4, a locking part forming portion 46 is provided on the end portion of the joint member 4 at the feeding member 2 side, and the external thread is formed on the outer surface of the locking part forming portion 46. When jointing the syringe as the feeding member 2 with the joint member 4, the tubular connecting portion 22 of the syringe is inserted into the joint member 4 and the joint member 4 is rotated, thereby screwing the locking part 51 as the external thread with the locked part 52 as the internal thread. The male luer tapered portion 22a of the tubular connecting portion 22 is subjected to luer taper connection with the inner tapered portion 42 of the joint member 4, and the end face 22c of the tubular connecting portion 22 abuts onto the end wall 44 of the joint member 4 and stops there. In this case, when locking of the locking part 51 with the locked part 52 is completed, the end face 22c of the tubular connecting portion 22 abuts onto the end wall 44 of the joint member 4, thereby making it possible to more securely prevent a clearance from being generated between the end wall 44 of the joint member 4 and the end face 22c of the tubular connecting portion 22 and to more securely prevent leakage of a liquid of a therapeutic substance. Further, when connecting the syringe to the joint member 4, it is not necessary to visually confirm whether or not there is a clearance between the end face 22c and the end wall 44 and to strongly press the syringe into the joint member 4 not to cause the clearance, and it can be surely recognized that the connecting operation has been completed. There may be a clearance between the end face 22c of the tubular connecting portion 22 and the end wall 44, and it is not necessarily required for the end face 22c to abut onto the end wall 44 and stop there. The above-mentioned effect can be obtained as long as a size of the clearance is such that retention of the therapeutic substance is not generated.

The connection between the joint member 4 and the catheter as the connected member 3 is performed by inserting the joint member 4 into the hub 33 of the catheter. When the joint member 4 is inserted into the hub 33, the outer tapered portion 43 of the joint member 4 is connected to the inner tapered connecting portion 32 of the hub 33 of the catheter by luer taper connection, thereby connecting the joint member 4 to the catheter. In this aspect, while the joint member 4 is connected to the catheter only by luer taper connection, it should be noted that the connection may be performed strongly by means of a lock mechanism in the same manner as in the connection of the joint member 4 to the syringe.

When the syringe is connected to the catheter via the joint member 4 and a catheter shaft 34 of the catheter is inserted into a body cavity, it is possible to feed the mixed liquid comprising the resin particles and the medicine from the distal end of the catheter into the body cavity by pushing the plunger 23 of the syringe. While generation of a dead space between the end face 22c of the tubular connecting portion 22 and the end wall 44 of the joint member 4 is inhibited as mentioned above, generation of a dead space between the tip end T of the joint member 4 and the inner tapered connecting portion 32 of the hub 33 of the catheter is also inhibited as mentioned above. Therefore, the resin particles contained in the mixed liquid are inhibited from remaining at the connecting places between the joint member 4 and the syringe and between the joint member 4 and the catheter, and the mixed liquid is fed smoothly into the body cavity via the catheter shaft 34. Accordingly, a precise amount of resin particles necessary for treatment can be introduced into the affected part. Further, it becomes easy to clean each member since retention of the resin particles at the connecting places caused by a dead space is inhibited.

Furthermore, generation of a dead space can be inhibited by using existing syringe and catheter and connecting the joint member 4 adapted to the taper angles of the syringe and catheter. Therefore, the joint member 4 has high versatility and assures easy handling.

Next, other aspects are explained by referring to FIGS. 5 and 6.

In the aspects shown in FIGS. 1 to 4, while the inner surface 41a of the communication channel 41 and the inner surface 22d of the tubular connecting portion 22 are configured so as to have substantially the same diameter, FIGS. 5 and 6 show other aspects where a diameter A of the end portion of the inner surface 22d of the tubular connecting portion 22 at the joint member 4 side is different from a diameter B of the end portion of the inner surface 41a of the communication channel 41 at the tubular connecting portion 22 side. With respect to the matters in common with the aspects shown in FIGS. 1 to 4, such as the connection structure between the joint member 4 and the connected member 3, hereinafter explanation thereof will be omitted and only differences are explained.

The second aspect shown in FIG. 5 illustrates an aspect in which the diameter A of the end portion of the inner surface 22d of the tubular connecting portion 22 at the joint member 4 side is larger than the diameter B of the end portion of the inner surface 41a of the communication channel 41 at the tubular connecting portion 22 side. As shown in FIG. 5, in the second aspect, the end wall 44 is formed in a shape tapered toward the connected member 3 side, and the communication channel 41 is configured so as to be in parallel with the insertion axis X and has the same diameter along the insertion axis X. In the second aspect, the end wall 44 and the end face 22c of the tubular connecting portion 22 are disposed apart from each other in the direction of the insertion axis X and do not abut to each other, however the end wall 44 and the end face 22c may abut to each other. In the second aspect, in the same manner as in the aspects shown in FIGS. 1 to 4, when the joint member 4 is connected to the hub 33, the inner end portion 45a of the opening 45 at the side of the connected member is disposed in proximity with and along the tapered surface of the inner tapered connecting portion 32 so that the tip end of the joint member 4 is located on the inner tapered connecting portion 32. Therefore, retention of the therapeutic substance at the end of the communication channel 41 at the connected member 3 side can be inhibited. Further, even if there is a dimensional variation in the tubular connecting portion 22, for example, the dimensional variation of the opening (diameter A), retention of the therapeutic substance is easily inhibited.

In the second aspect, the end wall 44 is formed in a tapered shape, and the communication channel 41 is configured so as to be in parallel with the insertion axis X and has the same diameter along the insertion axis X. However, unless the feeding of the therapeutic substance from the feeding channel 22e to the communication channel 41 is inhibited, the end wall 44 may be formed substantially vertical to the insertion axis X, or the communication channel 41 may be formed in a shape tapered toward the connected member 3 side. In addition, with respect to the end wall 44 and the inner surface 41a, a flow rate confirming portion formed in a shape tapered toward the connected member 3 side may be provided to enable the flow rate of the therapeutic substance fed from the feeding member 2 to be confirmed visually. The dimension of flow rate confirming portion is not limited particularly as long as the flow rate of the therapeutic substance can be confirmed. A position of the flow rate confirming portion with respect to the communication channel 41, an angle and a length of a slope with respect to the axis of the communication channel 41, a range of an inner diameter and the number of flow rate confirming portions to be provided can be set appropriately according to kind of a therapeutic substance. For example, the flow rate confirming portion with a slope having a given angle (e.g., 30°) with respect to the axis of the communication channel 41 and having a given length may be provided between the vertical end face 22c and the communication channel 41, or the end wall 44 may be formed in a tapered shape to be used as the flow rate confirming portion. In the case where the flow rate confirming portion is provided, the inner surface 41a of the communication path 41 may be either in parallel with the axis of the communication channel 41 or in a tapered shape with respect to the axis of the communication channel 41. By the flow rate confirming portion, the inflow of the therapeutic substance is easily confirmed. It is preferable that the angles of the end wall 44 and the communication channel 41 with respect to the axis of the communication channel 41 are those which enable retention of the therapeutic substance to be inhibited and are tapered toward the connected member 3 side.

The third aspect shown in FIG. 6 illustrates an aspect in which the diameter A of the end portion of the inner surface 22d of the tubular connecting portion 22 at the joint member 4 side is smaller than the diameter B of the end portion of the inner surface 41a of the communication channel 41 at the tubular connecting portion 22 side. As shown in FIG. 6, in the third aspect, the end wall 44 is formed substantially vertical to the insertion axis X, and the communication channel 41 is formed in a shape tapered toward the connected member 3 side. In FIG. 6, a part of the communication channel 41 at the feeding member 2 side is formed in a tapered shape, and the communication channel 41 at the connected member 3 side is formed in parallel with the insertion axis X. However, the entire communication channel 41 in a lengthwise direction along the insertion axis X may be in a tapered shape. In the third aspect, the end wall 44 and the end face 22c of the tubular connecting portion 22 are disposed apart from each other in the direction of the insertion axis X and do not abut to each other, however the end wall 44 and the end face 22c may abut to each other. In the third aspect, in the same manner as in the aspects shown in FIGS. 1 to 4 and the aspect shown in FIG. 5, when the joint member 4 is connected to the hub 33, the inner end portion 45a of an opening 45 at the side of the connected member is disposed in proximity with and along the tapered surface of the inner tapered connecting portion 32 so that the tip end of the joint member 4 is located on the inner tapered connecting portion 32. Therefore, retention of the therapeutic substance at the end of the communication channel 41 at the connected member 3 side can be inhibited. Further, even if there is a dimensional variation in the tubular connecting portion 22, for example, the dimensional variation of the opening (diameter A), retention of the therapeutic substance is easily inhibited.

In the third aspect, the end wall 44 is formed substantially vertical to the insertion axis X, and the communication channel 41 is formed in a tapered shape. However, unless the feeding of the therapeutic substance from the feeding channel 22e to the communication channel 41 is inhibited, the end wall 44 may be formed in a tapered shape toward the connected member 3 and the communication channel 41 may be formed so as to be in parallel with the insertion axis X and has the same diameter along the insertion axis X. Further, the both of the end wall 44 and the communication channel 41 may be formed in a tapered shape. In that case, it is preferable that the end wall 44 and the communication channel 41 are formed such that the angle between the end wall 44 and the insertion axis X is larger than the angle between the communication channel 41 and the insertion axis X.

EXPLANATION OF SYMBOLS 1 medical device
2 feeding member
21 body portion
22 tubular connecting portion
22a male luer tapered portion
22b opening
22c end face of a tubular connecting portion
22d inner surface of a tubular connecting portion
22e feeding channel
23 plunger
24 connecting portion
3 connected member
31 flow channel
32 inner tapered connecting portion
32a female luer tapered portion
32b inner tapered surface
33 hub
34 catheter shaft
4 joint member
41 communication channel
41a inner surface of a communication channel
42 inner tapered portion
43 outer tapered portion
44 end wall
45 opening at the side of a connected member
45a inner end portion of an opening at the side of a connected member
46 locking-part forming portion
5 lock mechanism
51 locking part
52 locked part
C connecting place
E end of an inner tapered connecting portion on a flow channel side
T tip end of a joint member
X insertion axis

What is claimed is:

1. A medical device comprising:
a feeding member comprising a tubular body portion being capable of containing a therapeutic substance to be fed into a body cavity and a tubular connecting portion provided at one end of the body portion and having a male luer tapered portion and an opening provided at a distal end of the male luer tapered portion to feed the therapeutic substance contained in the body portion;
a connected member having a flow channel through which the therapeutic substance fed from the feeding member passes and provided with a hub having an inner tapered connecting portion including a female luer tapered portion; and
a joint member connected to the tubular connecting portion of the feeding member and the hub of the connected member and having a communication channel for communicating the tubular connecting portion of the feeding member with the flow channel of the connected member,
wherein the joint member comprises an inner tapered portion for connecting to the male luer tapered portion, an outer tapered portion for connecting to the female luer tapered portion, and an opening at a side of the connected member for feeding the therapeutic substance from the feeding member to the connected member,
the tubular connecting portion has an end face being vertical to an axial direction of the tubular connecting portion at a free end of the tubular connecting portion,
the joint member has an abutting face connecting an end portion of the inner tapered portion at a connected member side to an end portion of an inner surface of the communication channel at a feeding member side,
the end face of the tubular connecting portion is in surface contact with the abutting face so that both the end face and abutting face are in surface contact throughout each face when the tubular connecting portion is pressed into the joint member along the inner tapered portion, and the inner surface of the communication channel and an inner surface of the tubular connecting portion have substantially the same diameter at a connecting place,
the outer tapered portion of the point member terminates at a tip end, the tip end including the opening at the side of the connected member, an outer most edge of the tip end forms an inner end portion of the opening of the joint member and is disposed so that the outer most edge of the tip end and the inner end portion of the opening are seated against an inner tapered surface of the female luer tapered portion of the inner tapered connecting portion so as to form a stepless interface between the inner end portion of the opening of the joint member and an end of the inner tapered connecting portion, and
when the joint member is connected to the hub, the tip end is located at a position apart from the end of the inner tapered connecting portion on the flow channel side toward the feeding member side.

2. The medical device of claim 1, wherein the joint member is formed from a resin or a metal.

3. The medical device of claim 1, wherein a lock mechanism is provided to the feeding member and/or the joint member, and when the feeding member and the joint member are locked by means of the lock mechanism, the end face of the tubular connecting portion abuts onto the abutting face of the joint member.

4. The medical device of claim 1, wherein the feeding member is a syringe, a three-way cock or a four-way cock, and the connected member is a catheter.

5. The medical device of claim 4, wherein the therapeutic substance is an intravascular embolization substance, the medical device is a medical device for vascular embolization for injecting the intravascular embolization substance into a body cavity, and the catheter is configured to be capable of feeding from the distal end of the catheter a mixed liquid contained in the syringe and comprising the intravascular embolization substance and a medicine.

* * * * *